United States Patent
Bowden (10) Patent No.: US 11,029,302 B2
(45) Date of Patent: Jun. 8, 2021

(54) LIQUID TREATMENT SYSTEM

(71) Applicant: Harvey Water Softeners Limited, Old Working (GB)

(72) Inventor: Harvey Bowden, Horsell (GB)

(73) Assignee: Harvey Water Softeners Limited, Old Working (GB)

( * ) Notice: Subject to any disclaimer, the term of this patent is extended or adjusted under 35 U.S.C. 154(b) by 0 days.

(21) Appl. No.: 16/598,541

(22) Filed: Oct. 10, 2019

(65) Prior Publication Data

US 2020/0041478 A1    Feb. 6, 2020

Related U.S. Application Data

(62) Division of application No. 15/691,990, filed on Aug. 31, 2017.

(51) Int. Cl.

| | |
|---|---|
| *G01N 33/18* | (2006.01) |
| *B01J 49/75* | (2017.01) |
| *C02F 1/42* | (2006.01) |
| *G01N 5/02* | (2006.01) |
| *G01N 30/96* | (2006.01) |
| *C02F 5/08* | (2006.01) |

(52) U.S. Cl.
CPC .......... *G01N 33/1853* (2013.01); *B01J 49/75* (2017.01); *C02F 1/42* (2013.01); *C02F 5/08* (2013.01); *C02F 2001/425* (2013.01); *C02F 2209/055* (2013.01); *C02F 2303/16* (2013.01); *C02F 2307/10* (2013.01); *G01N 5/02* (2013.01); *G01N 30/96* (2013.01)

(58) Field of Classification Search
None
See application file for complete search history.

(56) References Cited

U.S. PATENT DOCUMENTS

| | | | | |
|---|---|---|---|---|
| 4,298,468 | A | * 11/1981 | Heskett | ..... B01J 49/75 210/136 |
| 4,332,678 | A | * 6/1982 | Spiegl | ..... B01J 49/75 210/86 |

(Continued)

FOREIGN PATENT DOCUMENTS

| | | |
|---|---|---|
| DE | 2419031 A1 | 10/1975 |
| DE | 2953143 A1 | 10/1980 |

(Continued)

*Primary Examiner* — Jonathan M Peo
(74) *Attorney, Agent, or Firm* — Gable Gotwals (57) ABSTRACT

The present invention relates to a liquid treatment system having a sensor comprising a body, the body having a sensing material disposed therein, the sensing material being subject to a change in size in response to a composition of a liquid flowing therethrough; an actuating means disposed within the body and associated with the sensing material; wherein the actuating means is movable between a first position and a second position in response to the change in size of the sensing material to thereby mechanically actuate a switch member, such that when the actuating means is in the first position, flow of an actuating stream of the liquid is allowed by the switch member to thereby hydraulically actuate operation of the liquid treatment system; and when the actuating means is in the second position, flow of the actuating stream of the liquid is prevented by the switch member.

15 Claims, 7 Drawing Sheets

(56) References Cited

U.S. PATENT DOCUMENTS

| | | | | |
|---|---|---|---|---|
| 4,385,992 A | | 5/1983 | Clauer et al. | |
| 4,469,602 A | * | 9/1984 | Seal | C02F 1/42 |
| | | | | 210/140 |
| 4,668,386 A | * | 5/1987 | Seal | B01J 49/85 |
| | | | | 210/91 |

FOREIGN PATENT DOCUMENTS

| | | | | |
|---|---|---|---|---|
| DE | 3406724 A1 | 10/1985 | | |
| DE | 3831811 | 3/1990 | | |
| EP | 0240725 | 5/1987 | | |
| GB | 1454654 A | * 11/1976 | ............. | B01J 49/75 |
| GB | 1454654 A | 11/1976 | | |

* cited by examiner

LIQUID TREATMENT SYSTEM

CROSS REFERENCE TO RELATED APPLICATIONS

This application is a divisional application of U.S. application Ser. No. 15/691,990 filed Aug. 31, 2017 which is incorporated herein by reference.

FIELD OF THE INVENTION

The invention relates to a liquid treatment system including a device for initiating a liquid treatment process in said liquid treatment system, such as but not limited to a water softening system.

BACKGROUND OF THE INVENTION

Water softening systems such as ion exchange water softening systems have been developed and widely used in domestic homes of countries in which water having high minerals content, i.e. so called "hard water", is supplied. In general, a water softening system comprises a cylinder that carries out the "softening" process, i.e. the removal of the minerals such as calcium and magnesium ions from the water. In a typical ion exchange water softener, the cylinder contains a medium that performs ion exchange on the "hard water" by exchanging the "hard ions" such as calcium and magnesium ions with "soft ions" such as sodium or potassium ions. This medium may include an ion exchange resin, which contains and supplies a certain quantity of soft ions but has a higher affinity to the hard ions. When the "hard water" is made to pass through the ion exchange resins, the "hard ions" in the water will be replaced by the "soft ions" released from the resins, thereby "softens" the water.

When all the available "soft ions" have been replaced with "hard ions" after a prolonged use of the water softener, the resins have to be regenerated by eluting the calcium and magnesium ions with a solution of sodium chloride or sodium hydroxide, depending on the type of resins used. Particularly, in a traditional single cylinder water softener, the column of resins would have to be regenerated manually by first shutting off the water supply, opening the top of the cylinder, adding a measured amount of salt, closing the cylinder and then operating the valves to pass water through the column to allow the brine to carry out the ion exchange process. Over the years developments have been made and the valves can be automatically and electrically operated, but the frequency of regeneration still has to be done by guesswork or by manually reading a meter. Other water softeners have been made by adding meters into the system so that the water softeners will calculate when to regenerate. However, there exists many problems with this type of system as the regeneration has to be performed during the day when water is to be consumed, and thus a hard water bypass is required during the regeneration cycle. There are also sensor systems developed which measure the conductivity, or other signalling systems arranged within the resin bed to establish when to regenerate. But again the regeneration has to take place during daytime when water is on demand.

To overcome these shortcomings, twin cylinders water softeners have been developed with various control mechanisms. These are known as duplex water softeners. However, many of such water softener systems fail to accurately predict the hardness of the water which varies by region and by period over the year; for example, the hardness may vary between summer and winter, etc.

More recently, sensor systems which utilise the expansion and contraction of resin during the regeneration cycle and measure the size difference between the regenerated state and the exhausted state of the resin have been made available. These sensors are mounted outside the water softener cylinder and a water sample is taken at a point within the cylinder for testing and thus establishing when the cylinder is about to run out and that a regeneration is required. These sensors are operated electrically, with a number of valves being electrically controlled to carry out the regeneration. Regeneration can be performed either immediately during service by use of a bypass, or during the night when there is little water consumption. If the cylinder is allowed to regenerate during the night, a reserve capacity will be required which results in a loss of efficiency.

All of the aforementioned systems require the user's input in establishing the frequency of regeneration, and very often, the column of the water softener will be deliberately overly regenerated to ensure that sufficiently softened water can be supplied to the customer. When the household circumstances change and the number of people increases or decreases, the majority of available water softener systems needs to be recalibrated to take this into account. Also, when the water hardness varies by region or by period over the year, once again the systems have to be recalibrated. If no recalibration is done, the water softening efficiency will be affected and the increase in water hardness may degrade parts of the water softener system such as the valves, as well as to other household appliances in contact with the hard water.

OBJECTS OF THE INVENTION

An object of the present invention is to provide a device for use in a liquid treatment system, in which the aforesaid shortcomings are mitigated or at least to provide a useful alternative.

The above object is met by the combination of features of the main claims; the sub-claims disclose further advantageous embodiments of the invention.

One skilled in the art will derive from the following description other objects of the invention. Therefore, the foregoing statements of object are not exhaustive and serve merely to illustrate some of the many objects of the present invention.

SUMMARY OF THE INVENTION

In a first main aspect of the present invention, there is provided a sensing device for use in a liquid treatment system. The sensing device comprises a body having a sensing material disposed therein, the sensing material being subject to a change in size in response to a composition of a liquid flowing therethrough. The sensing device further comprises an actuating means disposed within the body and associated with the sensing material, wherein the actuating means is movable between a first position and a second position in response to the change in size of the sensing material to thereby mechanically actuate a switch member, such that, when the actuating means is in the first position, a flow of an actuating stream of the liquid is allowed by the switch member to thereby hydraulically actuate operation of the liquid treatment system; and when the actuating means is in the second position, a flow of the actuating stream of the liquid is prevented by the switch member.

In a second main aspect of the present invention, there is provided a liquid treatment system comprising at least one liquid treatment tank and at least one sensing device according to the first main aspect.

In a third main aspect of the present invention, there is provided a liquid treatment system. The liquid treatment system comprises a liquid treatment tank; a sensing material disposed within the liquid treatment tank, with the sensing material being subject to a change in size in response to a composition of a liquid flowing therethrough. The liquid treatment system further comprises an actuating means associated with the sensing material; wherein the actuating means is movable between a first position and a second position in response to the change in size of the sensing material to thereby mechanically control operation of an actuating stream outlet, such that, when the actuating means is in the first position, a flow of an actuating stream of the liquid via the actuating stream outlet is allowed to thereby hydraulically actuate operation of the liquid treatment system; and, when the actuating means is in the second position, a flow of the actuating stream of the liquid via the actuating stream outlet is prevented.

In a fourth main aspect of the present invention, there is provided a method of initiating a liquid treatment process. The liquid treatment process comprises the steps of: providing a sensing material inside a liquid treatment tank, the sensing material being subject to a change in size in response to a composition of a liquid flowing therethrough; arranging an actuating means in association with the sensing material, the actuating means being movable in response to the change in size of the sensing material; and allowing flow of an actuating stream of the liquid in response to a mechanical movement of the actuating means to thereby hydraulically actuate operation of the liquid treatment system.

In a fifth main aspect of the present invention, there is provided a mechanically operable switch member. The switch member comprises an actuating means movable between a first position and a second position in response to a change of an operating condition; and a stopper member movable between an open position and a closed position in response to movement of the actuating means; wherein the actuating means comprises a first magnetic member adapted to magnetically interact with a second magnetic member provided at the stopper member, such that when the actuating means is movable from the first position to the second position, a decrease in magnetic attraction between the first and the second magnetic members causes the stopper member to move from the open position to the closed position The summary of the invention does not necessarily disclose all the features essential for defining the invention; the invention may reside in a sub-combination of the disclosed features.

BRIEF DESCRIPTION OF THE DRAWINGS

The foregoing and further features of the present invention will be apparent from the following description of preferred embodiments which are provided by way of example only in connection with the accompanying figures, of which.

DESCRIPTION OF PREFERRED EMBODIMENTS

The following description is of preferred embodiments by way of example only and without limitation to the combination of features necessary for carrying the invention into effect.

Reference in this specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

Referring to FIGS. 1 to 6, illustrated is a sensing device or sensor 10 for use in a liquid treatment system, and particularly, but not exclusively, to a water softening system which "softens" hard water by removing the "hard" ions such as calcium ions and magnesium ions from the water during an ion exchange process. The sensor 10 is capable of determining when the ion exchange capacity of the ion exchange materials is depleted and thus a regeneration of the ion exchange materials is required, and subsequently, automatically and preferably mechanically only actuating the regeneration process in a hydraulic manner without requiring an electrical input to the system. In this embodiment, the sensor 10 is preferred to be arranged within a cylinder of the water softening system where the ion exchange process takes place, and particularly, to be positioned at the top of the cylinder of the water softening system.

Figure 1:
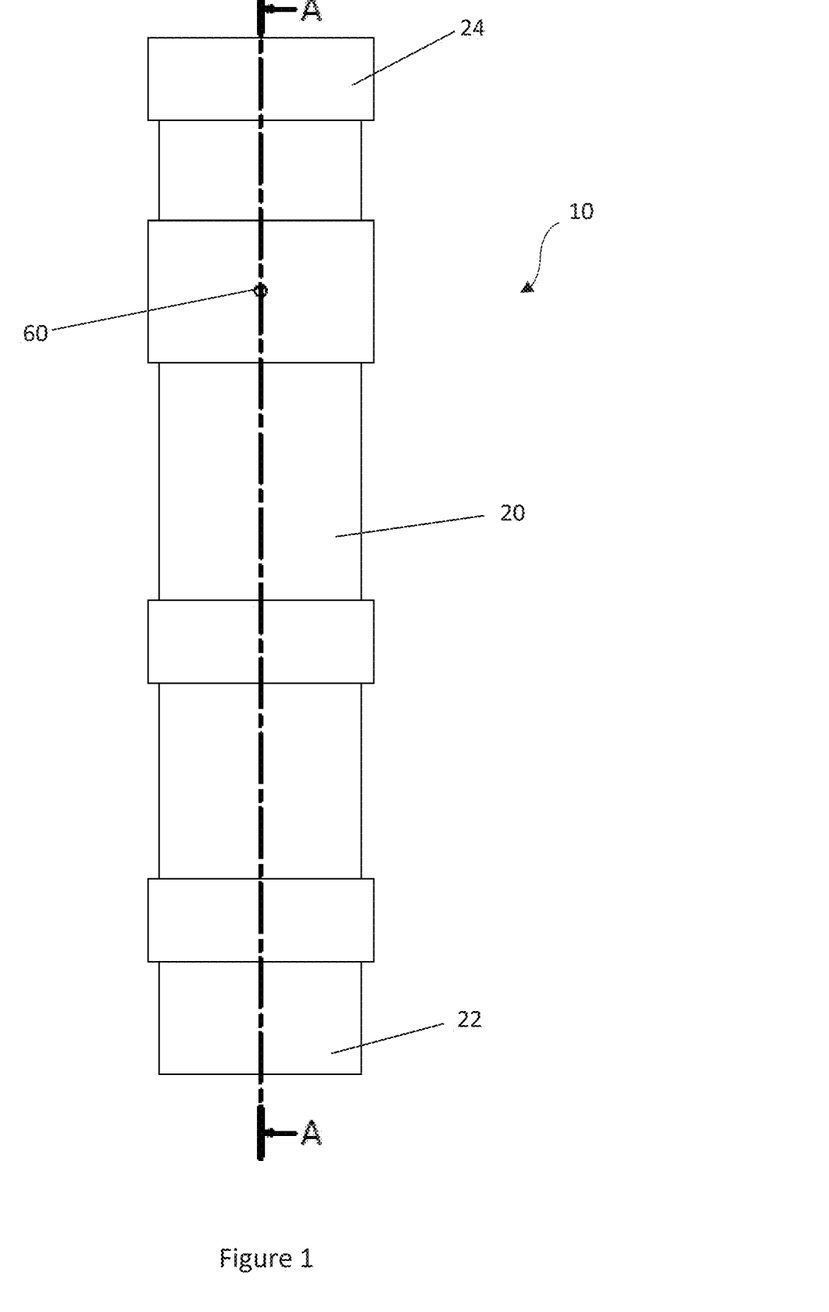
FIG. 1 is a schematic diagram showing a sensing device for use in a water softening system according to an embodiment of the present invention.
Figure 2:
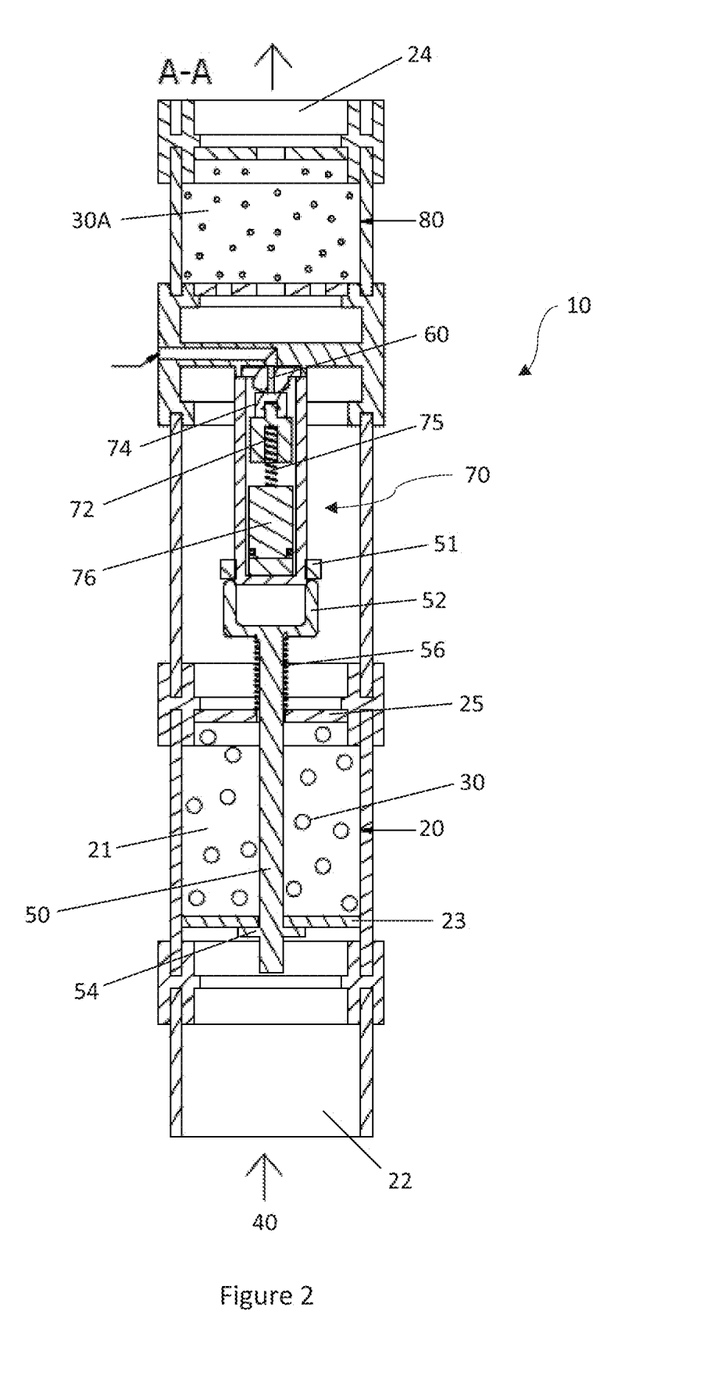
FIG. 2 is a cross-sectional view along the line A-A of the sensing device of FIG. 1.
Figure 3:
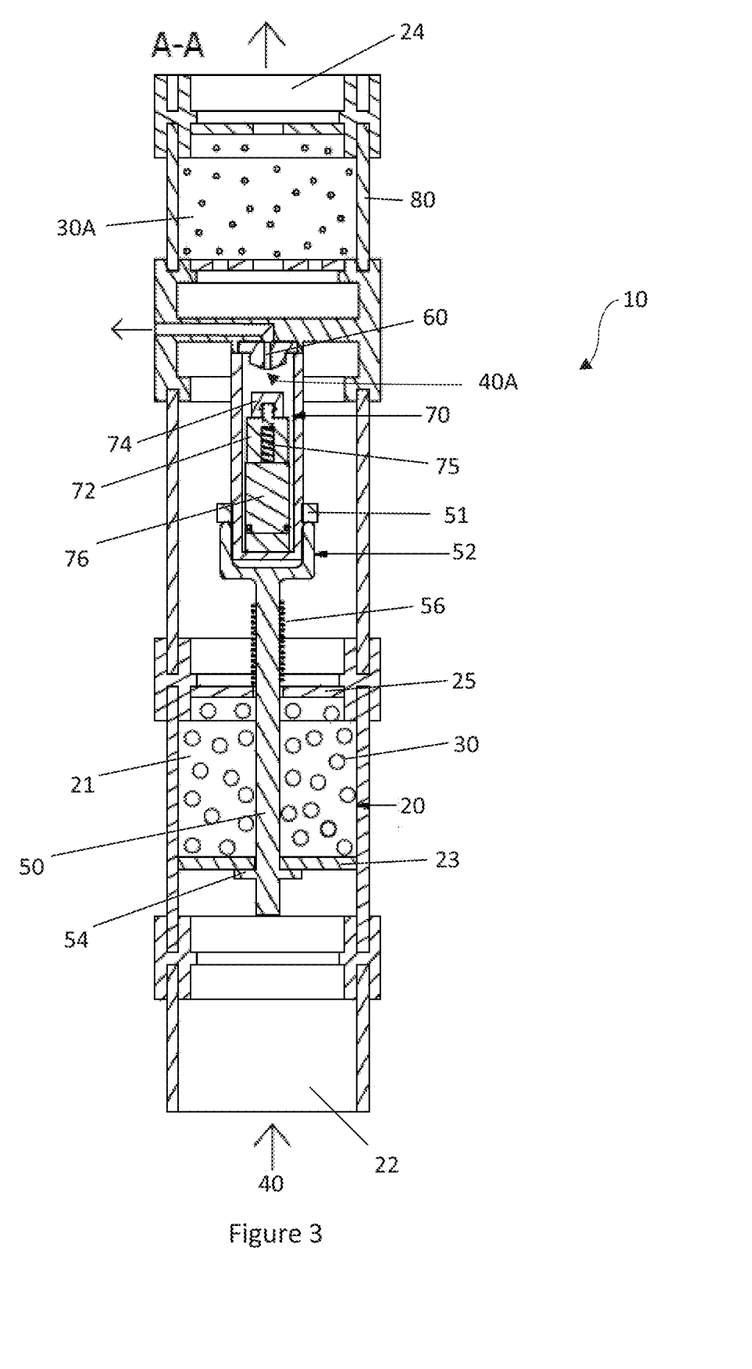
FIG. 3 is a cross sectional view along the line A-A of the sensing device of FIG. 1 in a configuration which detects that the water softening system requires regeneration and actuating the regeneration.

FIGS. 1 to 3 show an embodiment of a sensor 10 according to the present invention. The sensor 10 comprises a body 20 having a column of sensing material 30 disposed therein. The body 20 includes at least one liquid inlet 22 adapted to receive liquid 40 into the body 20, and at least one liquid outlet 24 adapted to eject the liquid 40 after it passes through the column of sensing material 30 within the body 20. In the embodiment as shown in the figures, the sensing material column 30 is positioned between the liquid inlet 22 and the liquid outlet 24, with the liquid inlet 22 and the liquid outlet 24 being in fluid communication through the column of sensing material. It is preferred that the liquid outlet 24 is arranged at a higher position relative to the liquid inlet 22, for example, with the liquid inlet 22 being positioned at the bottom portion of the body 20, and the liquid outlet 24 being positioned at the top portion of the body 20, allowing an upward flow of the liquid 40 so as to facilitate a more efficient ion exchange process.

The sensing materials 30 are subject to a change in size in response to the ionic composition of the liquid 40 flowing therethrough. Specifically, the sensing materials 30 may comprise one or more types of ion exchange resins preferably having a low cross linkage. The ion exchange resins may comprise crosslinked resins, with their size changing capacities varying with and/or depending on the respective degree of crosslinking in the resin composition. For example, a resin with a lower degree of crosslinking will demonstrate a greater change in size during the ions depletion and regeneration processes. In one embodiment, the crosslinked resins of the sensing materials 30 can be provided in the form of small beads each having a diameter ranged from 0.35 mm to 2 mm, for example. Specifically, the size and the shape of the resin beads may vary according to the ionic state of the resins. For example, the resin beads may shrink and thus reduce in size over the course of the ion exchange process when the sodium or potassium ions of the resins are depleted; and may expand to substantially restore the original size of the resin beads when they are regenerated. The regeneration of the resins can be conducted by, for example, washing of the resins with a solution with a high concentration of sodium ions such as a concentrated salt water, e.g. brine.

In the embodiment as shown in FIGS. 2-3, the sensing materials 30 of the sensor 10 are adapted to be accommodated in a chamber 21 defined by two screen members 23, 25 and the inner wall of the body 20. Specifically, the screen members 23, 25 are provided with liquid passageways such as pores of sufficiently small sizes which allow only a liquid such as the liquid 40 to pass through but prevent the resin beads of the sensing materials 30 escaping. Particularly, the screen member 25 is preferred to be fixedly connected at the body 20, while the screen member 23 is movable relative to the body 20 and is associated with an actuating means 50 disposed within the body 20. In one embodiment, the actuating means 50 may comprise at one end an abutting member 54 adapted to abut the screen member 23, and an actuating member 52 at the other end which is adapted to mechanically actuate a switch member 70. The switch member 70 is mechanically operable to initiate the regeneration process of the water softening system in a hydraulic manner without requiring an electrical input to the system.

Specifically, the actuating means 50 is associated with (i.e. via the engagement of the screen member 12 and the abutting member 54) and is movable in response to the size change of the sensing materials 30 between a first, actuating position and a second, standby position, which are illustrated in FIG. 3 and FIG. 2, respectively. In the first, actuating position as shown in FIG. 3, the sensing materials 30 are in a contracted state and regeneration of the ion exchange column 30 is initiated. In the second, standby position as shown in FIG. 2, the sensing materials 30 are in an expanded state and no regeneration process of the ion exchange column 30 is actuated. In these embodiments, the abutting member 54 of the actuating means 50 is biased by a resilient member 56 such as a spring member towards the first, actuating position, and therefore, when the ion exchange resins 30 are in the depleted, contracted state, the abutting member 54 will be automatically moved towards the first, actuating position under the action of the spring member 50, as shown in FIG. 3. On the other hand, when the ion exchange resins 30 are in the charged, expanded state, the force of the expanded resins will be applied on the screen member 23 to move away from the screen member 25 and thus pushing the abutting member 54 backward to position the actuating means 50 in the second, standby position, as shown in FIG. 2.

Preferably, movement of the actuating means 50 between the first and the second positions based on the physical state of the sensing materials 30 will in turn actuate mechanically the switch member 70 to initiate a regeneration process of the water softening system in preferably a hydraulic manner. In one embodiment, the switch member 70 may comprise a switch housing 71 with its external surface being engageable by the actuating member 52 of the actuating means 50, and preferably lightly engageable by the actuating member 52. Specifically, the switch housing 71 defines an internal cavity which is capable of accommodating a stopper member 74 movable between an open position and a closed position: at the open position, the stopper member 74 is arranged to be spaced away from and thereby to unblock or open an actuating outlet 60 via which a hydraulic signal can be sent to initiate the regeneration process of the water softening system; while at the closed position, the stopper member 74 is adapted to engage and thus to block or close the actuating outlet 60 to thereby prevent passage of any hydraulic signal and thus, prevent initiation of the regeneration process. As shown in FIGS. 2 and 3, the stopper member 74 can be configured to comprise, or to be provided with, a magnetic member 72, with movement of the stopper member 74 and the magnetic member 72 being biased towards the closed position under the action of a spring 75 connected to member 76.

Preferably, the actuating outlet 60 is in fluid communication with the liquid inlet 22 and the liquid outlets 24, and more preferably, s positioned at an upper portion of the sensing device 10. In one embodiment, the actuating outlet 60 is arranged to allow an actuating stream 40a of the liquid 40 to flow out of the body 20 and subsequently to trigger a series of hydraulic actuations of the water softening system thereby activating the resin regeneration process. For example, when the actuating means 50 is in the second, stand by position (see FIG. 2), the actuating outlet 60 is blocked by the stopper member 74 and thus a flow of the actuating stream 40a of the liquid 40 through the actuating outlet 60 is prevented. No hydraulic actuation of the regeneration process can therefore be triggered. On the other hand, when the actuating means 50 is in the first, actuating position (see FIG. 3), the stopper member 74 is released from the actuating outlet 60. The actuating stream 40a of the liquid 40 is then allowed to flow through the actuating outlet 60 to hydraulically actuate the regeneration process of water softening system. Accordingly, the actuation of the regeneration process can be solely triggered mechanically followed by liquid flow and the pressure developed by the liquid flow, without any electrical input to the sensor, the switch or the water softening system being required and without any electrical actuation of the sensor, the switch or the water softening system being required. Details of the actuating liquid flow paths and the regeneration processes will be described below.

In one embodiment, the mechanical actuation of the switch member 70 can be assisted by magnetic interaction. For example, after a prolonged use of the water softening system where the soft ions of the ion exchange column are depleted and thus the sensing materials 30 are in a contracted state as shown in FIG. 3, the absence of an expansion force at the chamber 21 causes the screen member 23 to move towards the screen member 25. Subsequently, the abutting means 54 and thus the actuating means 50 will be movable from the second position to the first position, causing the actuating member 52 to approach the stopper member 74. The actuating member 52 at its distal end, for example, is preferably provided with a magnetic member 51 such as a magnetic ring member 51. Movement of the magnetic ring member 51 towards the stopper member 74 will therefore increase the magnetic interaction therebetween, i.e. the magnetic attraction between the magnetic member 72 of the stopper member 74 and the magnetic ring member 51 of the actuating member 52. The growing magnetic attraction between the two magnetic members 72, 51 will cause the stopper member 74 to move from the closed position to the open position, thereby releasing the actuating outlet 60 to allow an actuating stream of liquid to hydraulically actuate a regeneration process of the water softening system.

The regeneration process of the ion exchange column 30 causes the sensing materials to resume their expanded state thereby causing the actuating means 50 and thus the actuating member 52 to mechanically move from the first position to the second position. A decrease in magnetic attraction between the magnetic member 72 of the stopper member 74 and the magnetic ring member 51 of the actuating member 52 causes the stopper member 74 to move from the open position to the closed position, thus closing the actuating outlet 60. No passage of an actuating stream of the liquid is therefore allowed and therefore, the initiation of the regeneration process is prevented.

Optionally, a secondary, regenerating resins 30A containing chamber 80 can be provided to "soften" any hard water breakthrough from the ion exchange column 30, i.e. when the resins of the ion exchange column are fully depleted and thus fail to soften any further liquid 40 passing up and therethrough, and prior to the actuation of the regeneration process to regenerate the column 30. In this situation, the secondary regeneration column 30A serves as a safeguard to prevent any hard water from leaving the liquid outlet 24.

Figure 4:
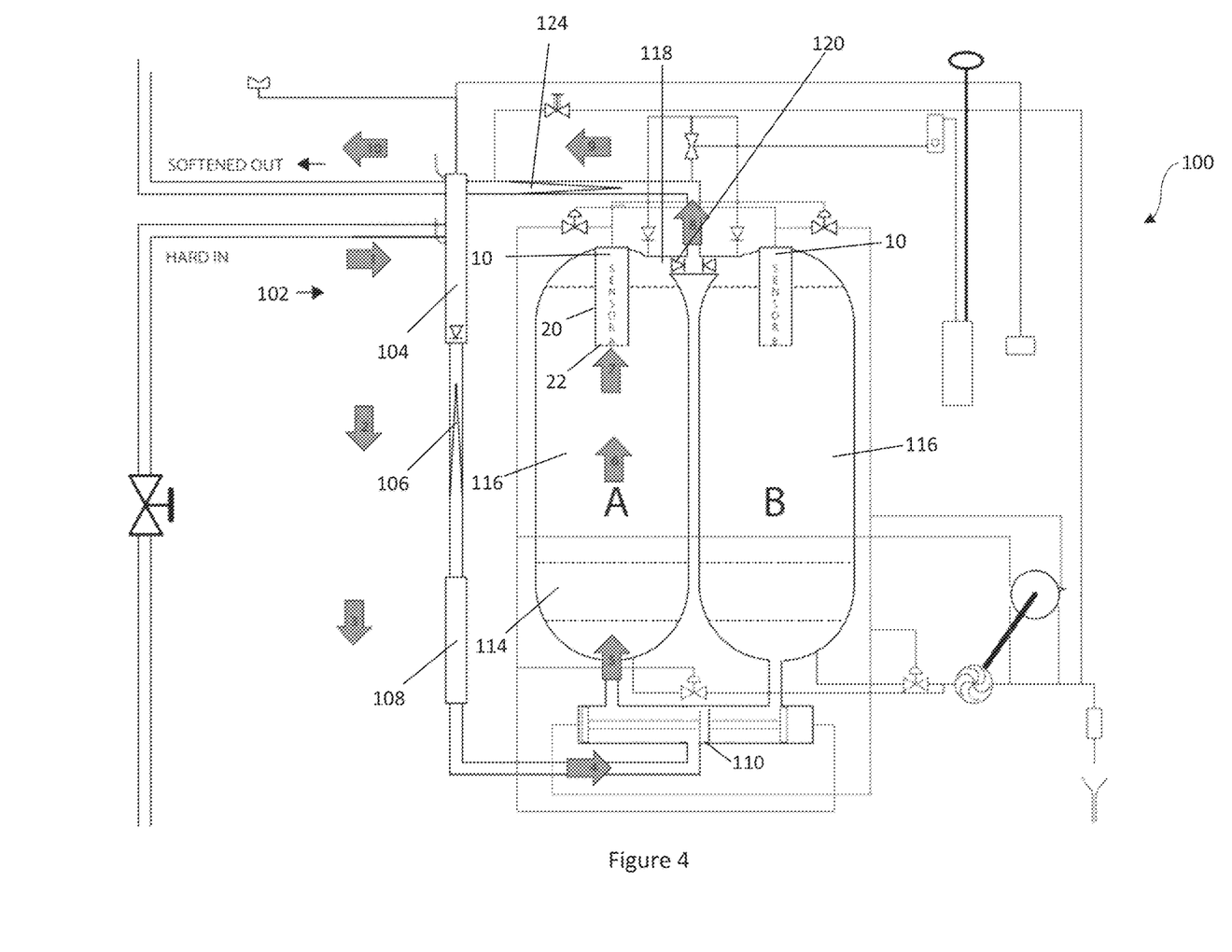
FIG. 4 is a flow diagram showing a water softening system with the sensing device according to the invention in the operating condition shown in FIG. 2.

The detailed sensing and actuating or initiating process of a water softening system 100 by the sensor 10 is further illustrated in the flow diagram as shown in FIG. 4.

Specifically, the system 100 embodies a twin-cylinder/tank system which comprises a Cylinder A having a Sensor A within and at the top of the cylinder for detecting the depletion of the water softening capacity (i.e. the ion exchange capacity) of said cylinder; and a Cylinder B having a Sensor B within and at the top of the cylinder for detecting the depletion of the water softening capacity (i.e. the ion exchange capacity) of said cylinder. When Cylinder A is on its functional, water-softening operation, Cylinder B will be allowed to be on a standby mode, and vice versa. With such an arrangement, when the ion exchange column of Cylinder A is depleted and thus a regeneration is required, Cylinder B can be made to become operational so as to allow a continual supply of softened water, and thus no interruption to the soft water supply will be caused whenever a regeneration to a column is required.

As illustrated in FIG. 4, during a normal operation of the water softening system 100, a flow of hard water 102 (as indicated by Arrow 1) will enter a bypass 104 with a valve arrangement which may include a non-return valve. The hard water 102 will then travel through an inlet strainer 106 (see Arrow 2) where debris from the water 102 is removed. The system 100 includes an inlet pressure limiting valve (PLV) 108 which monitors the inlet pressure and ensures that the system 100 works under an optimum maximum water pressure. Alternatively, the PLV can also be arranged upstream of the bypass 104.

As shown by Arrow 4, the hard water 102 will proceed to travel through a diverter valve 110 which diverts the inlet water into either water softening Cylinder A or water softening Cylinder B. In the scenario as shown in the figure, the water flow is diverted to Cylinder A. Particularly, the hard water flow enters Cylinder A via the cylinder inlet at the bottom of the cylinder (see Arrow 5) and which will subsequently pass through a bed of treatment materials 114 which may include carbon. The carbon bed 114 pre-treats the water by, for example, removing any chlorine presents in the water 102 in order to protect the resins in the cylinder and the sensor 10. After passing through the carbon bed 114, the water will continue to flow in an upflow direction (see Arrow 6) through a resin bed 116 where the water-softening ion exchange process will take place. The resins of the resin bed 116 may include the same or different resins compositions to those of the sensing materials 30 in the sensor 10.

As the water front rises through the resin bed 116 inside the cylinder, it will eventually reach the bottom of the sensor 10 (see Arrow 7) and will enter the body 20 of the sensor 10 via the liquid inlet 22. The liquid inlet 22 can be sitting on, or preferably, positioned below the upper surface of the resins bed 116 so that the hard water will enter the sensor 10 and thereby be detected by the sensing materials 30 of the sensor 10 prior to the exhaustion of the resins bed 116. At the beginning of the service run of the water softening system 100, the hard water 102 can be sufficiently softened by the ion exchange resins as it travels through the resins bed 116 inside the cylinder, with a portion of the softened water running into the sensor 10 via the sensor inlet 22, and another portion of the softened water continuing to rise up the cylinder and eventually leaving the cylinder via the cylinder outlet 118, which is equipped with an outlet non-return valve 120. Within the sensor 10, the softened water will not cause any conformational change to the sensing materials 30 (not shown). The actuating means 50 will remain in its second, standby position as illustrated in FIG. 2, with the stopper member 74 being remained in blocking the actuating outlet 60. No regeneration process will thus be actuated.

After leaving the cylinder from the cylinder outlet 118 (see Arrow 8), the softened water will continue to travel through a filter 124 which prevents any resins from escaping from the cylinder to the service pipeline which may otherwise block the pipeline (see Arrow 9). The filter 124 may include an outlet strainer of about 80 microns in size. The softened water will then exit the water softening system 100 to service (see Arrow 10).

Figure 5:
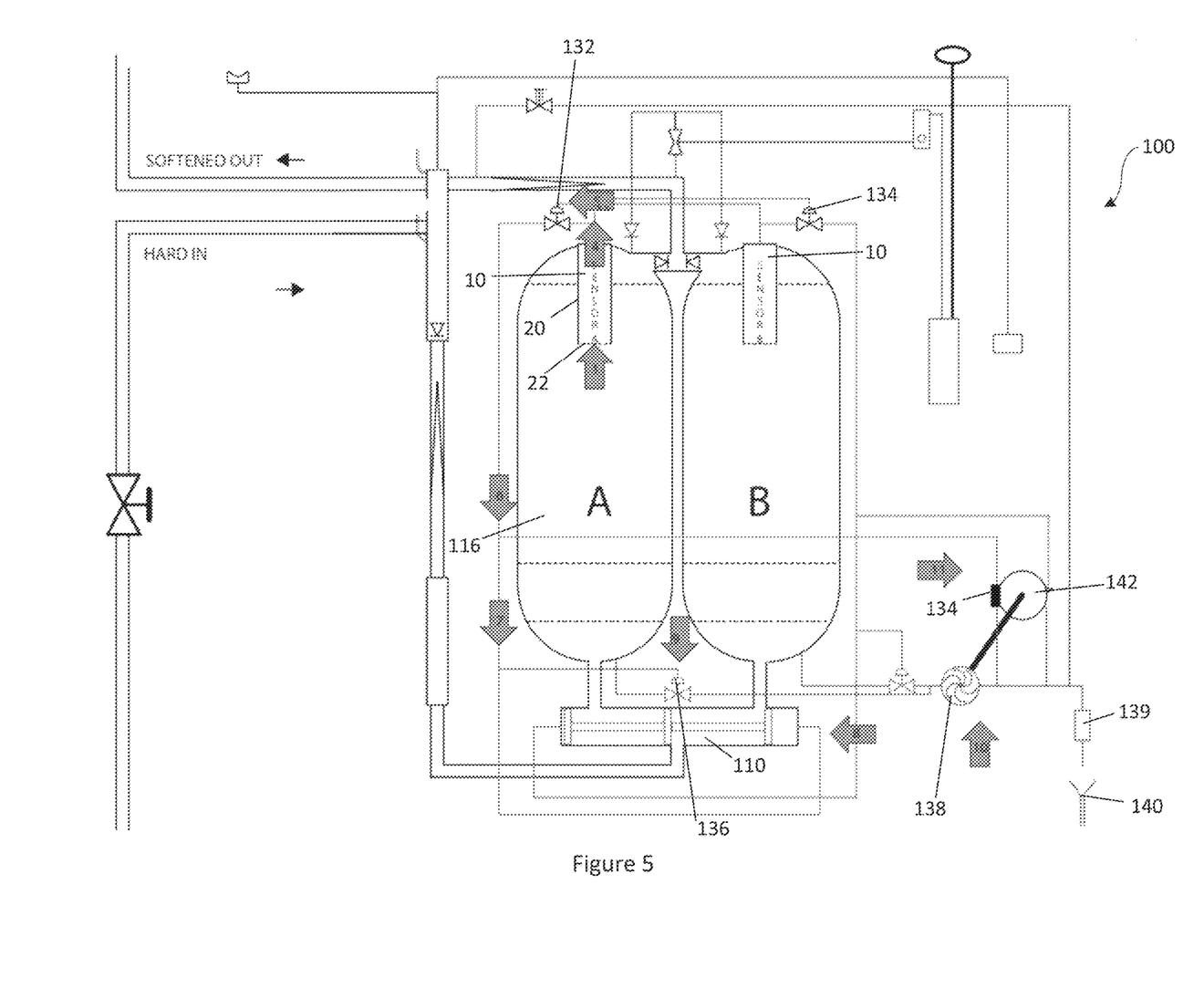
FIG. 5 is a flow diagram showing a water softening system with the sensing device according to the invention in the operating condition shown in FIG. 3.

However, after a prolonged operation of the water softening system 100, the resins in the resins bed 116 will start to deplete and as a result, hard water would not be sufficiently "softened" and the hardness will rise up the cylinder. The process of detecting the water hardness and the subsequent actuation of the regeneration process is illustrated in FIG. 5. As the hardness front rises through the resin bed 116 of Cylinder A, it will eventually reach the liquid inlet 22 at the bottom of the sensor 10. The liquid inlet 22 can be sitting on, or preferably, positioned below the upper surface of the resins bed 116 so that the hard water will enter the sensor 10 and thereby be detected by the sensing materials 30 of the sensor 10 prior to the exhaustion of the resins bed 116. More preferably, the bottom portion of the sensor body 20 is at least partially embedded into the resins bed 116. The ratio of the embedded portion to the non-embedded portion of the sensor 10 can be selected or calculated for facilitating the most efficient sensing of the water hardness prior to the exhaustion of the resins bed 116.

As the hard water enters the body 20 of the sensor 10 (see Arrow 11), the hardness of the water will cause the sensing materials 30 of the sensor 10 to shrink. The shrinkage may cause the resins of the sensing materials 30 to reduce in size by approximately 50% (v/v) thus rendering the actuating means 50 to move from the second position to the first position, which results in the release of the actuating outlet 60 by the stopper member 74, as shown in FIG. 3. The unblocking of the actuating outlet 60 allows a flow of the actuating stream of water 40a from the sensor 10 which initiates a hydraulic pilot signal to trigger the regeneration process of the water softening column 116 (see Arrow 12). As further indicated by Arrow 13, the actuating liquid stream 40a will flow out of the actuating outlet 60 and pass through an interlock valve 132. The interlock valve 132 will only open to allow the signal flow provided the other cylinder, i.e. Cylinder B, is not attempting to regenerate and that the interlock valve 134 is closed.

The signal stream will continue to flow as indicated by Arrow 14, which will then split into two separate paths: a first flow path which sends a signal (as indicated by Arrow 15) to a regeneration stop valve 134; and a second flow path (as indicated by Arrow 16) which sends another signal to the diverter valve 110 and also the regeneration start valve 136. The pressure on the diverter valve 110 closes its connection with Cylinder A (as indicated by Arrow 17) and allows the inlet water to flow into Cylinder B for the ion exchange process. At the same time, the regeneration start valve 136 opens to allow a volume of regenerating liquid (e.g. salt water) which has just passed through and regenerated the ion exchange column 116, to exit Cylinder A Formation of the regenerating liquid and the introduction of regenerating liquid into Cylinder A will be discussed in the next paragraph below. The salt water will flow through a regeneration meter 138 which measures the volume of water running to the drain 140 (as indicated by Arrow 18). The regeneration meter 138 is connected with a regeneration CAM 142 which is adapted to rotate in accordance with the regeneration meter 138 and, after the running of a pre-determined volume of water into the drain 140, the regeneration stop valve 134 opens to release the hydraulic pressure in the signal line, and thus stops the regeneration process.

Figure 6:
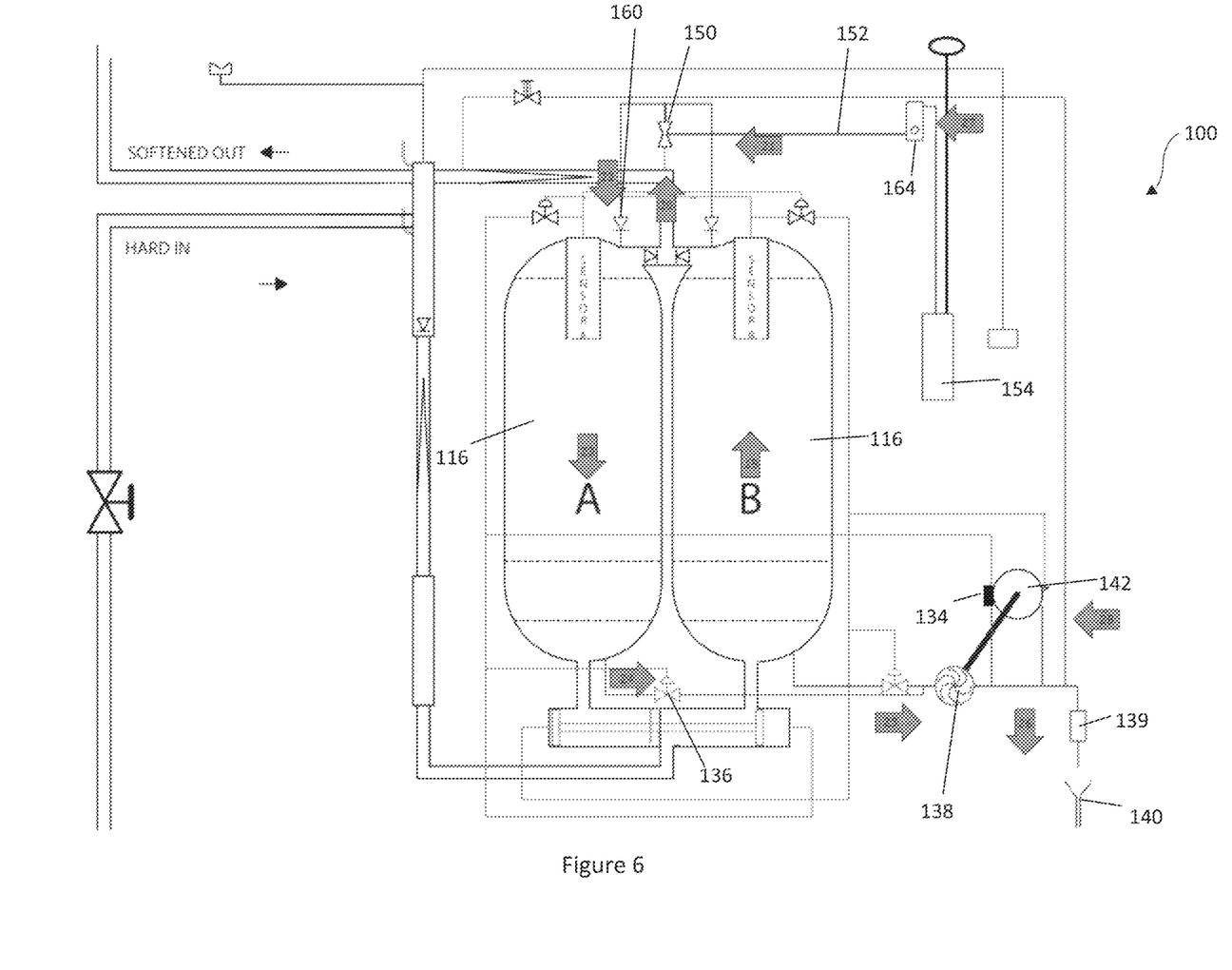
FIG. 6 is a flow diagram showing a regeneration process of the water softening system.

As described earlier, when hard water is detected by Sensor A such that a regeneration process is actuated, the service flow will be diverted to Cylinder B by the action of the diverter valve 110. As shown in FIG. 6, the water will be allowed to flow upward along the ion exchange column 116 of Cylinder B where hardness of the water is softened by the action of ion exchange resins (see Arrow 19). The softened water will then leave Cylinder B (see Arrow 20) via the cylinder outlet at the top of the cylinder, and a proportion of the flow will be diverted to a venture valve 150 where it initiates a suction action on a brine line 152 (see Arrow 21). The suction on the brine line 152 draws a flow of brine solution via a brine valve 154, which controls the supply of the brine solution from a brine tank (not shown). A portion of the softened water from Cylinder B will then mix with the brine solution in a pre-determined ratio to form the regenerating liquid, and the regenerating liquid then will be fed through a brine inlet valve 160 into Cylinder A (see Arrow 22) to regenerate the resins bed 116. The regenerating brine mixture will run down the cylinder to wash through the resins bed 116, during which the sodium ions of the brine mixture will recharge the depleted resins through an ion exchange reaction (as indicated by Arrow 23).

After washing and thus regenerating the resins bed 116, the brine mixture, which is now composed of a lower level of sodium ions, will exit Cylinder A via the regeneration start valve 136 as mentioned earlier (see Arrow 24). The regenerating effluent will be measured by the regeneration meter 138 (see Arrow 25), and then will pass to the drain 140 via a drain block 139 (see Arrow 26).

Referring again to the brine line 152 and the brine valve 154, when the brine solution from the salt tank is exhausted, air will enter into the brine pipe which will then rise to the air check 164 so that no more brine solution or air can enter Cylinder A. After the supply of the brine solution is prevented, only the softened water from Cylinder B will be allowed to run into Cylinder A, thereby rinsing the regenerated resins column 116 to remove any residual salts that may be left over from the previous washing process by the regenerating liquid. The rinsing effluent will also be measured by the regeneration meter 138, and after a pre-determined volume of the rinsing effluent is measured, the regeneration CAM 142 will rotate to open the regeneration stop valve 134 which releases the signal pressure from the pipeline (see Arrow 28). The regeneration start valve 136 then closes to thereby prevent further water flows from Cylinder A into the drain 140. Cylinder A will then sit on standby until Cylinder B needs to be regenerated.

Figure 7:
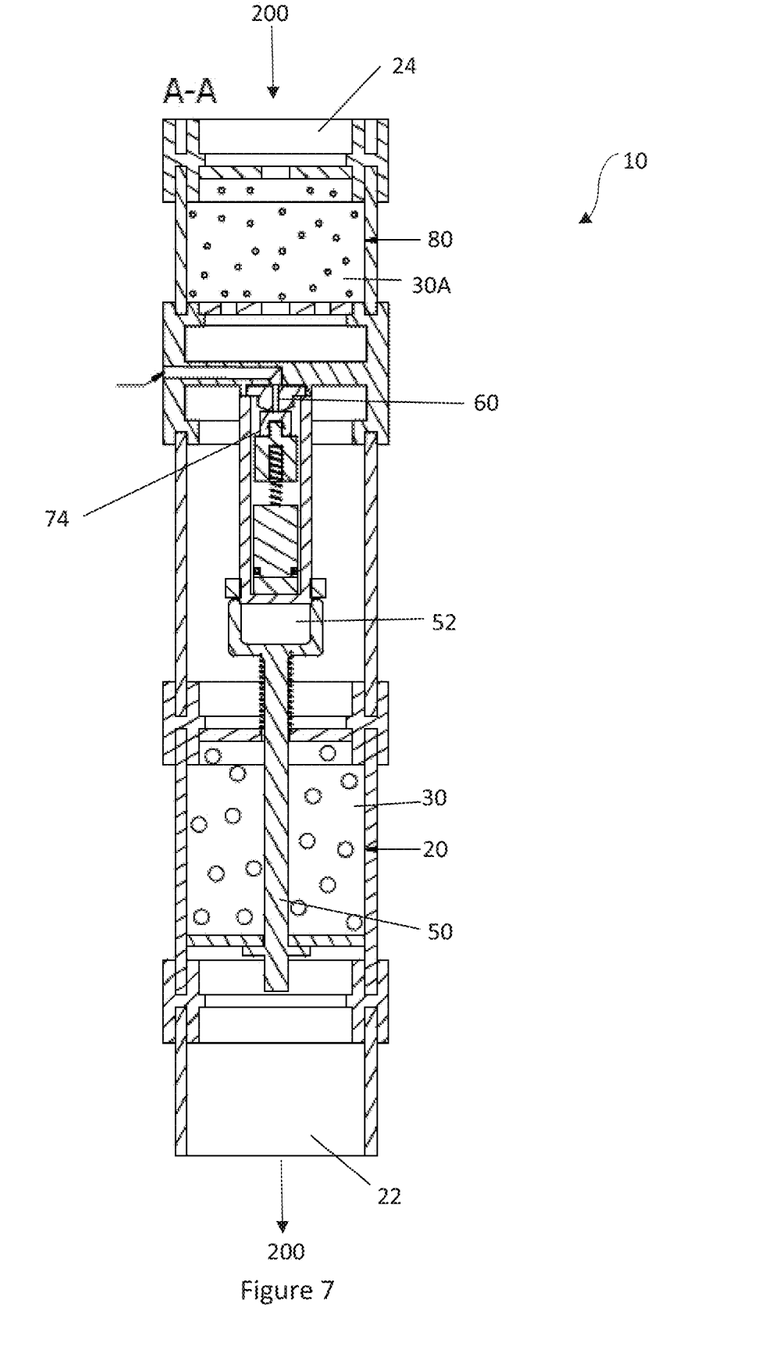
FIG. 7 is a schematic diagram of the sensor device during a regeneration process as shown in FIG. 6.

When Cylinder A is undergoing a regenerating process of the ion exchange bed 116, Sensor A which is located within Cylinder A will also be simultaneously regenerated. The configuration of sensor 10 during this regeneration process is illustrated in FIG. 7. Particularly, when the regenerating brine solution is introduced into Cylinder A during the regenerating process, Sensor 10 of Cylinder A will also receive a flow of the regenerating brine solution 200 via the liquid outlets 24. The brine solution 200 will flow downward and along the sensor body 20 to regenerate the sensing materials 30 (optionally, 30A), and eventually leave the body 20 via the liquid inlet 22. On completion of the regenerating process of the sensor 10, the sensing materials 30 will expand and be restored to substantially their original size, with the resultant hydraulic pressure therein pushing the actuating means 50 downwards. Downward movement of the actuating member 52 will close the actuating outlet 60 by releasing the stopper member 74, so that, when the regeneration stop valve 134 opens, the actuating signal depressurizes in the pipeline and thus no water will flow into the drain 140. This is the end of the regeneration cycle.

When the regeneration process is completed, the brine valve 154 will open to refill the brine tank with water coming from the venture valve 150. When a pre-determined volume of water is filled into the brine tank, the brine valve 154 will be closed so that brine solution of a specific concentration can be prepared for the next regenerating cycle.

Although a twin-cylinders/tanks system comprising Cylinder A and Cylinder B, with each cylinder having an individual sensor (i.e. Sensor A and Sensor B, respectively) is described and illustrated, a person skilled in the art would appreciate that the present invention should not be limited to a twin-cylinders system. Instead, it will be understood that a single cylinder water softening system having a sensor therein, or a multiple-cylinders system with each cylinder having an individual sensor therein, is also encompassed within the scope of the invention.

The present invention also relates to a method of method of initiating a liquid treatment process, and particularly, for sensing when a regeneration of an ion exchange column of a water softening system is required, and subsequently, actuating the regenerating process. The method comprises the steps of providing a sensing material inside a liquid treatment tank, the sensing material being subject to a change in size in response to a composition of a liquid flowing therethrough; arranging an actuating means in association with the sensing material, the actuating means being movable in response to the change in size of the sensing material; and allowing flow of an actuating stream of the liquid in response to a mechanical movement of the actuating means to thereby hydraulically actuate operation of the liquid treatment system. No step of providing of an electrical input is required for this process.

The present invention further relates to a mechanically operable switch member. The switch member comprises an actuating means movable between a first position and a second position in response to a change of an operating condition; a stopper member movable between an open position and a closed position in response to movement of the actuating means; wherein the actuating means comprises a first magnetic member adapted to magnetically interact with a second magnetic member provided at the stopper member, such that when the actuating means is movable from the first position to the second position, there is a decrease in magnetic attraction between the first and the second magnetic members.

The present invention is advantageous in that it provides a sensor or sensing device which is capable of detecting when a regeneration of the ion exchange column is required, and subsequently, actuating solely mechanically the regenerating process by means of hydraulic pressure, without the need of any electricity supply or electrical input which is essential in the prior art. The sensor is incorporated within the cylinder of the water softening system where the ion exchange takes place, with the sensor being preferably held at the top of the cylinder and at least partially embedded in the ion exchange column of the cylinder, so that any hard water can be detected by the sensor before the exhaustion of the ion exchange resins. Specifically, with this arrangement the sensing materials of the sensor are placed in the same flow of liquid with the ion exchange column of the cylinder, thereby allowing a more efficient detection of the ion exchange capacity of the water softening system by the sensor.

As mentioned earlier, both the detection and the actuation of the regeneration process is to be operated automatically and mechanically. No pre-programming to the system or adjustment to, for example, the amount of salts in preparing brine solution of a suitable concentration, is required. In addition, no adjustment will be required during installation by the engineers or operation by the consumers. If the type of salt being used changes which causes a change in the concentration of the brine solution, or if the hardness of the water changes due to weather or regional variations, the sensor is capable of taking these changes into account and initiating the regeneration process with suitable adjustments accordingly and automatically. This facilitates optimum salt efficiency to be obtained, by regenerating the column with a low level of salt and a modest capacity for the service run so that efficiency can be maximized. For example, efficiencies of between 20-50% can be achieved by the sensor equipped water softening system as embodied in the present invention, when compared with known systems currently in the marketplace.

The twin-cylinders/tanks system as embodied in the present invention also allows a continual supply of softened water to the consumers, with no interruption to the water supply being caused when regeneration of the ion exchange column is required at one cylinder. Specifically, when one cylinder is operating to soften the incoming water, the other cylinder will be allowed to standby or if necessary, undergo a regenerating process without affecting the normal operation of the water softening system. Again, the shifting between an operating mode and a standby mode of the two cylinders are fully automatic and are controlled solely in a hydraulic manner, without the need of any electricity input.

The invention claimed is:

1. A liquid treatment system, comprising:
   a liquid treatment tank including a resin bed, the resin bed treating liquid inside the liquid treatment tank;
   a sensing material disposed within the liquid treatment tank, the sensing material being subject to a change in size in response to a composition of the liquid flowing therethrough;
   an actuating member movable between a first position and a second position in response to the change in size of the sensing material to thereby mechanically control operation of an actuating stream outlet, such that, when the actuating member is in the first position, flow of an actuating stream of the liquid via the actuating stream outlet is allowed to thereby hydraulically actuate operation of the liquid treatment system; and, when the actuating member is in the second position, flow of the actuating stream of the liquid via the actuating stream outlet is prevented, the actuating member being movable between the first position and the second position along an axis axially aligned with the actuating stream outlet; and
   a switch member operable with the actuating member; wherein the switch member is adapted to open the actuating stream outlet when the actuating member is in the first position, and is adapted to close the actuating stream outlet when the actuating member is in the second position;
   wherein the actuating member comprises a first magnetic member adapted to magnetically interact with a second magnetic member provided at the switch member, such that, when the actuating member is moved from the second position to the first position, the first magnetic member is moved axially towards the second magnetic member along the axis axially aligned with the actuating stream outlet and the switch member is drawn axially away from the actuating stream outlet.

2. The liquid treatment system according to claim 1, wherein operation of the liquid treatment system is adapted to be actuated without a need of an electricity supply.

3. The liquid treatment system according to claim 1, wherein the actuating member is mechanically operated in response to the change in size of the sensing material to hydraulically actuate operation of the liquid treatment system, the arrangement being such that there is no need for any electrical or electronic actuation of the liquid treatment system.

4. The liquid treatment system according to claim 1, wherein the actuating member is in the first position when the sensing material is in a contracted state, and is in the second position when the sensing material is in an expanded state.

5. The liquid treatment system according to claim 1, further comprising a resilient member adapted to bias the actuating member towards the first position.

6. The liquid treatment system according to claim 1, wherein the sensing material and the actuating member are accommodated in a body and wherein said body comprises a liquid inlet adapted to receive the liquid when a sensing device is in a first operation, and is adapted to eject the liquid when the sensing device is in a second operation.

7. The liquid treatment system according to claim 6, wherein the body further comprises a liquid outlet adapted to eject the liquid when the sensing device is in the first operation, and is adapted to receive the liquid when the sensing device is in the second operation.

8. The liquid treatment system according to claim 7, wherein the liquid inlet is arranged at a lower position relative to the liquid outlet.

9. The liquid treatment system according to claim 6, wherein the liquid inlet is arranged on or below an upper surface of the resin bed of the liquid treatment system.

10. The liquid treatment system according to claim 9, wherein the sensing device is at least partially embedded in the resin bed.

11. The liquid treatment system according to claim 6, wherein the body is positioned within the liquid treatment tank of the liquid treatment system.

12. The liquid treatment system according to claim 11, wherein the sensing device is arranged at a top portion of the liquid treatment tank of the liquid treatment system.

13. The liquid treatment system according to claim 9, wherein the body is adapted to actuate regeneration of the resin bed when the actuating member is in the first position.

14. The liquid treatment system according to claim 1, wherein, when the first magnetic member is moved axially towards the second magnetic member along the axis axially aligned with the actuating stream outlet, the switch member is drawn axially away from the actuating stream outlet and towards the first magnetic member.

15. The liquid treatment system according to claim 14, wherein the switch member is drawn axially away from the actuating stream outlet and towards the first magnetic member against the bias of a spring.

\* \* \* \* \*